(12) United States Patent
Rowland et al.

(10) Patent No.: US 9,721,463 B2
(45) Date of Patent: *Aug. 1, 2017

(54) WIRELESS SENSOR READER

(71) Applicant: Endotronix, Inc., Woodridge, IL (US)

(72) Inventors: Harry Rowland, Plainfield, IL (US);
Roger Watkins, Dunlap, IL (US);
Balamurugan Sundaram, Peoria, IL (US)

(73) Assignee: Endotronix, Inc., Woodbridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,054

(22) Filed: Mar. 29, 2016

(65) Prior Publication Data

US 2016/0210846 A1    Jul. 21, 2016

Related U.S. Application Data

(63) Continuation of application No. 13/859,444, filed on Apr. 9, 2013, now Pat. No. 9,305,456, which is a
(Continued)

(51) Int. Cl.
*G08C 17/02* (2006.01)
*G08B 13/14* (2006.01)
(Continued)

(52) U.S. Cl.
CPC ............ *G08C 17/02* (2013.01); *A61B 5/0031* (2013.01); *A61B 5/0215* (2013.01);
(Continued)

(58) Field of Classification Search
CPC ................................. G08B 23/00; G08C 17/02
(Continued)

(56) References Cited

U.S. PATENT DOCUMENTS 3,714,595 A * 1/1973 Denenberg ........... H03D 1/2236
329/356
3,872,455 A    3/1975 Fuller et al.
(Continued)

FOREIGN PATENT DOCUMENTS

CN    101116322    1/2008
HK    1147906    8/2011
(Continued)

OTHER PUBLICATIONS

Extended European Search Report, Endotronix, Inc., Application No. 10762085.8-2319/2417590, Jan. 4, 2013.
(Continued)

*Primary Examiner* — Joseph Feild
*Assistant Examiner* — John Mortell
(74) *Attorney, Agent, or Firm* — McDonald Hopkins LLC

(57) ABSTRACT

A wireless sensor reader is provided to interface with a wireless sensor. The wireless sensor reader transmits an excitation pulse to cause the wireless sensor to generate a ring signal. The wireless sensor reader receives and amplifies the ring signal and sends the signal to a phase-locked loop. A voltage-controlled oscillator in the phase-locked loop locks onto the ring signal frequency and generates a count signal at a frequency related to the ring signal frequency. The voltage-controlled oscillator is placed into a hold mode where the control voltage is maintained constant to allow the count signal frequency to be determined.

20 Claims, 7 Drawing Sheets

Related U.S. Application Data continuation of application No. 13/423,693, filed on Mar. 19, 2012, now Pat. No. 8,432,265, which is a continuation of application No. 12/419,326, filed on Apr. 7, 2009, now Pat. No. 8,154,389, which is a continuation-in-part of application No. 12/075,858, filed on Mar. 14, 2008, now abandoned.

(60) Provisional application No. 60/918,164, filed on Mar. 15, 2007.

(51) Int. Cl.
    *A61B 5/00*           (2006.01)
    *A61B 5/0215*       (2006.01)

(52) U.S. Cl.
    CPC .......... *A61B 5/6882* (2013.01); *A61B 5/7225* (2013.01); *A61B 2562/0219* (2013.01)

(58) Field of Classification Search
    USPC .................................................... 340/870.02
    See application file for complete search history.

(56) References Cited

U.S. PATENT DOCUMENTS

| | | |
|---|---|---|
| 3,888,708 A | 6/1975 | Wise et al. |
| 3,943,915 A | 3/1976 | Severson |
| 4,023,562 A | 5/1977 | Hynecek et al. |
| 4,026,276 A | 5/1977 | Chubbuck |
| 4,037,324 A | 7/1977 | Andreasen |
| 4,067,235 A | 1/1978 | Markland et al. |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson et al. |
| 4,511,858 A | 4/1985 | Charavit et al. |
| 4,531,526 A | 7/1985 | Genest |
| 4,567,459 A | 1/1986 | Folger et al. |
| 4,644,420 A | 2/1987 | Buchan |
| 4,815,472 A | 3/1989 | Wise et al. |
| 4,881,410 A | 11/1989 | Wise et al. |
| 4,953,387 A | 9/1990 | Johnson et al. |
| 4,966,034 A | 10/1990 | Bock et al. |
| 5,005,577 A | 4/1991 | Frenkel |
| 5,006,819 A | 4/1991 | Buchan et al. |
| 5,013,396 A | 5/1991 | Wise et al. |
| 5,046,497 A | 9/1991 | Millar |
| 5,055,838 A | 10/1991 | Wise et al. |
| 5,059,543 A | 10/1991 | Wise et al. |
| 5,108,420 A | 4/1992 | Marks |
| 5,113,868 A | 5/1992 | Wise et al. |
| 5,227,798 A * | 7/1993 | Hildebrand ........... G01S 13/753 342/44 |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |
| 5,334,952 A | 8/1994 | Maddy et al. |
| 5,343,064 A | 8/1994 | Spangler et al. |
| 5,377,524 A | 1/1995 | Wise et al. |
| 5,417,235 A | 5/1995 | Wise et al. |
| 5,564,434 A | 10/1996 | Halperin et al. |
| 5,581,248 A | 12/1996 | Spillman, Jr. et al. |
| 5,690,674 A | 11/1997 | Diaz |
| 5,872,520 A * | 2/1999 | Seifert ............... G06K 19/0723 340/5.61 |
| 5,920,233 A | 7/1999 | Denny |
| 5,992,769 A | 11/1999 | Wise et al. |
| 6,015,386 A | 1/2000 | Kensey et al. |
| 6,025,725 A | 2/2000 | Gershenfeld et al. |
| 6,109,113 A | 8/2000 | Chavan et al. |
| 6,111,520 A | 8/2000 | Allen et al. |
| 6,126,675 A | 10/2000 | Shchervinsky et al. |
| 6,140,144 A | 10/2000 | Najafi et al. |
| 6,174,322 B1 | 1/2001 | Schneidt |
| 6,190,400 B1 | 2/2001 | Van De Moer et al. |
| 6,206,835 B1 | 3/2001 | Spillman, Jr. et al. |
| 6,232,150 B1 | 5/2001 | Lin et al. |
| 6,278,379 B1 | 8/2001 | Allen et al. |
| 6,287,256 B1 | 9/2001 | Park et al. |
| 6,309,350 B1 | 10/2001 | VanTassel et al. |
| 6,331,163 B1 | 12/2001 | Kaplan |
| 6,338,284 B1 | 1/2002 | Najafi et al. |
| 6,359,444 B1 * | 3/2002 | Grimes .................... H01Q 9/28 324/633 |
| 6,447,449 B1 | 9/2002 | Fleischman et al. |
| 6,454,720 B1 | 9/2002 | Clerc et al. |
| 6,459,253 B1 | 10/2002 | Krusell |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fisher et al. |
| 6,636,769 B2 | 10/2003 | Govari et al. |
| 6,645,143 B2 | 11/2003 | VanTassel et al. |
| 6,647,778 B2 | 11/2003 | Sparks |
| 6,658,300 B2 | 12/2003 | Govari et al. |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,713,828 B1 | 3/2004 | Chavan et al. |
| 6,749,622 B2 | 6/2004 | McGuckin, Jr. et al. |
| 6,764,446 B2 | 7/2004 | Wolinsky et al. |
| 6,779,406 B1 | 8/2004 | Kuzina et al. |
| 6,783,499 B2 | 8/2004 | Schwartz |
| 6,805,667 B2 | 10/2004 | Christopherson et al. |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,923,625 B2 | 8/2005 | Sparks |
| 6,926,670 B2 | 8/2005 | Rich et al. |
| 6,932,114 B2 | 8/2005 | Sparks |
| 6,935,010 B2 | 8/2005 | Tadigadpa et al. |
| 6,939,299 B1 | 9/2005 | Petersen et al. |
| 6,945,939 B2 | 9/2005 | Turcott |
| 6,959,608 B2 | 11/2005 | Bly et al. |
| 6,968,743 B2 | 11/2005 | Rich et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,013,734 B2 | 3/2006 | Zdeblick et al. |
| 7,025,727 B2 | 4/2006 | Brockway et al. |
| 7,028,550 B2 | 4/2006 | Zdeblick et al. |
| 7,048,756 B2 | 5/2006 | Eggers et al. |
| 7,059,176 B2 | 6/2006 | Sparks |
| 7,059,195 B1 | 6/2006 | Liu et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,192,001 B2 | 3/2007 | Wise et al. |
| 7,198,603 B2 | 4/2007 | Penner et al. |
| 7,211,048 B1 | 5/2007 | Najafi et |
| 7,228,735 B2 | 6/2007 | Sparks et al. |
| 7,245,117 B1 | 7/2007 | Joy et al. |
| 7,273,457 B2 | 9/2007 | Penner |
| 7,284,442 B2 | 10/2007 | Fleischman et al. |
| 7,290,454 B2 | 11/2007 | Liu |
| 7,425,200 B2 | 9/2008 | Brockway et al. |
| 7,432,723 B2 | 10/2008 | Ellis et al. |
| 7,466,120 B2 | 12/2008 | Miller et al. |
| 7,483,805 B2 | 1/2009 | Sparks et al. |
| 7,498,799 B2 | 3/2009 | Allen et al. |

(56) References Cited

U.S. PATENT DOCUMENTS

| | | | |
|---|---|---|---|
| 7,550,978 B2 | 6/2009 | Joy et al. | |
| 7,641,619 B2 | 1/2010 | Penner | |
| 7,647,831 B2 | 1/2010 | Corcoran et al. | |
| 7,679,355 B2 | 3/2010 | Allen et al. | |
| 7,686,762 B1 | 3/2010 | Najafi et al. | |
| 7,686,768 B2 * | 3/2010 | Bodecker | A61B 5/0031 600/374 |
| 7,839,153 B2 | 11/2010 | Joy et al. | |
| 7,936,174 B2 | 5/2011 | Ellis et al. | |
| 8,154,389 B2 | 4/2012 | Rowland et al. | |
| 8,360,984 B2 | 1/2013 | Yadav et al. | |
| 8,432,265 B2 | 4/2013 | Rowland et al. | |
| 8,493,187 B2 | 7/2013 | Rowland et al. | |
| 8,852,099 B2 | 10/2014 | Von Arx et al. | |
| 2002/0045921 A1 | 4/2002 | Wolinsky et al. | |
| 2002/0072656 A1 | 6/2002 | Vantassel et al. | |
| 2002/0115920 A1 | 8/2002 | Rich et al. | |
| 2002/0138009 A1 | 9/2002 | Brockway et al. | |
| 2002/0151816 A1 | 10/2002 | Rich et al. | |
| 2002/0177782 A1 | 11/2002 | Penner | |
| 2002/0188207 A1 | 12/2002 | Richter | |
| 2003/0062957 A1 | 4/2003 | Terashima et al. | |
| 2003/0136417 A1 | 7/2003 | Fonseca et al. | |
| 2003/0139677 A1 | 7/2003 | Fonseca et al. | |
| 2003/0139771 A1 | 7/2003 | Fisher et al. | |
| 2003/0158584 A1 | 8/2003 | Cates et al. | |
| 2003/0191496 A1 | 10/2003 | Edwards et al. | |
| 2004/0102806 A1 | 5/2004 | Broome et al. | |
| 2004/0158138 A1 | 8/2004 | Kilcoyne et al. | |
| 2004/0220637 A1 | 11/2004 | Zdeblick et al. | |
| 2004/0255643 A1 | 12/2004 | Wise et al. | |
| 2004/0260164 A1 | 12/2004 | Kilcoyne et al. | |
| 2005/0013685 A1 | 1/2005 | Ricketts et al. | |
| 2005/0015014 A1 | 1/2005 | Fonseca et al. | |
| 2005/0043601 A1 | 2/2005 | Kilcoyne et al. | |
| 2005/0049634 A1 | 3/2005 | Chopra | |
| 2005/0080346 A1 | 4/2005 | Gianchandani et al. | |
| 2005/0090719 A1 | 4/2005 | Scheiner et al. | |
| 2005/0103114 A1 | 5/2005 | Bly et al. | |
| 2005/0145187 A1 * | 7/2005 | Gray | A01K 11/008 119/174 |
| 2005/0154321 A1 | 7/2005 | Wolinsky et al. | |
| 2005/0160825 A1 | 7/2005 | Zdeblick et al. | |
| 2005/0160827 A1 | 7/2005 | Zdeblick et al. | |
| 2005/0187482 A1 | 8/2005 | O'Brien et al. | |
| 2005/0228308 A1 | 10/2005 | Iddan et al. | |
| 2005/0288596 A1 | 12/2005 | Eigler et al. | |
| 2005/0288604 A1 | 12/2005 | Eigler et al. | |
| 2005/0288722 A1 | 12/2005 | Eigler et al. | |
| 2006/0047205 A1 | 3/2006 | Ludomirsky et al. | |
| 2006/0052821 A1 | 3/2006 | Abbott et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0085039 A1 * | 4/2006 | Hastings | A61N 1/0587 607/9 |
| 2006/0116590 A1 | 6/2006 | Fayram et al. | |
| 2006/0122522 A1 | 6/2006 | Chavan et al. | |
| 2006/0129050 A1 | 6/2006 | Martinson et al. | |
| 2006/0161171 A1 | 7/2006 | Schwartz | |
| 2006/0177956 A1 | 8/2006 | O'Brien et al. | |
| 2006/0178583 A1 | 8/2006 | Montegrande et al. | |
| 2006/0178695 A1 | 8/2006 | Decant, Jr. et al. | |
| 2006/0196277 A1 | 9/2006 | Allen et al. | |
| 2006/0206146 A1 | 9/2006 | Tenerz | |
| 2006/0212047 A1 | 9/2006 | Abbott et al. | |
| 2006/0217762 A1 | 9/2006 | Meahs et al. | |
| 2006/0217763 A1 | 9/2006 | Abbott et al. | |
| 2006/0217764 A1 | 9/2006 | Abbott et al. | |
| 2006/0229488 A1 | 10/2006 | Ayre et al. | |
| 2006/0241354 A1 | 10/2006 | Allen | |
| 2006/0244465 A1 | 11/2006 | Kroh et al. | |
| 2006/0271078 A1 | 11/2006 | Modesitt | |
| 2006/0287602 A1 | 12/2006 | O'Brien et al. | |
| 2007/0007240 A1 | 1/2007 | Wise et al. | |
| 2007/0028698 A1 | 2/2007 | Guziak et al. | |
| 2007/0032734 A1 | 2/2007 | Najafi et al. | |
| 2007/0049980 A1 | 3/2007 | Zielinski et al. | |
| 2007/0049984 A1 | 3/2007 | Osypka | |
| 2007/0060959 A1 | 3/2007 | Salo et al. | |
| 2007/0073351 A1 | 3/2007 | Zielinski et al. | |
| 2007/0088388 A1 | 4/2007 | Opolski et al. | |
| 2007/0096715 A1 | 5/2007 | Joy et al. | |
| 2007/0100215 A1 | 5/2007 | Powers et al. | |
| 2007/0106246 A1 | 5/2007 | Modesitt | |
| 2007/0106328 A1 | 5/2007 | Wardle et al. | |
| 2007/0106333 A1 | 5/2007 | Fernandez | |
| 2007/0112358 A1 | 5/2007 | Abbott et al. | |
| 2007/0118039 A1 | 5/2007 | Bodecker et al. | |
| 2007/0149880 A1 | 6/2007 | Willis | |
| 2007/0160748 A1 | 7/2007 | Schugt et al. | |
| 2007/0210786 A1 | 9/2007 | Allen et al. | |
| 2008/0281212 A1 * | 11/2008 | Nunez | A61B 5/0031 600/508 |
| 2009/0115396 A1 | 5/2009 | Allen et al. | |
| 2009/0224773 A1 | 9/2009 | Joy et al. | |
| 2009/0224837 A1 | 9/2009 | Joy et al. | |
| 2010/0026318 A1 | 2/2010 | Kroh et al. | |
| 2010/0161004 A1 | 6/2010 | Najafi et al. | |
| 2010/0308974 A1 | 12/2010 | Rowland et al. | |
| 2012/0286934 A1 | 11/2012 | Rowland et al. | |

FOREIGN PATENT DOCUMENTS

| | | | |
|---|---|---|---|
| JP | 2000-517073 | 12/2000 | |
| JP | 2006-512112 | 4/2006 | |
| JP | 2007-210547 | 8/2007 | |
| JP | 2008-532590 | 8/2008 | |
| WO | 2004045407 | 6/2004 | |
| WO | WO 2004045407 A1 * | 6/2004 | A61B 5/11 |
| WO | 2005/107583 | 11/2005 | |
| WO | 2006/070278 | 7/2006 | |
| WO | 2006070278 | 7/2006 | |
| WO | WO 2006070278 A1 * | 7/2006 | G06Q 20/28 |
| WO | 2006096582 | 9/2006 | |
| WO | WO 2006096582 A1 * | 9/2006 | A61B 5/0002 |
| WO | 2006/130488 | 12/2006 | |
| WO | 2007/030489 | 3/2007 | |
| WO | 2008/115456 | 9/2008 | |
| WO | 2010/117356 | 10/2010 | |
| WO | 2010/117597 | 10/2010 | |

OTHER PUBLICATIONS

International Preliminary Report on Patentability, Endotronix, Inc., PCT/US2012/034979, Nov. 7, 2013.

International Search Report and the Written Opinion of the International Searching Authority, Endotronix, Inc., PCT/US2012/34979, Nov. 2, 2012.

International Preliminary Report on Patentability, Nunez, Anthony, I. et al., PCT/US2008/003475, Sep. 24, 2009.

International Search Report and the Written Opinion of the International Searching Authority, Endotronix, Inc., PCT/US2009/39730, Jun. 30, 2009.

International Search Report and the Written Opinion of the International Searching Authority, Endotronix, Inc., PCT/US2010/27951, Aug. 25, 2010.

International Search Report and the Written Opinion of the International Searching Authority, Nunez, Anthony I, PCT/US2008/03475, Aug. 4, 2008.

Collins, Carter, Miniature Passive Pressure Transensor for Implanting in the Eye, Transactions on Bio-Medical Engineering, vol. BME-14, No. 2, pp. 74-83, Apr. 1967.

Nagumo, J., Uchiyama, A, Kimoto, S., Watanuki, T., Hori, M., Suma, K, Ouchi, A., Kumano, M., and Watanabe, H., Echo Capsule for Medical Use (A Batteryless Endoradiosonde), IRE Transaction on Bio-Medical Electronics, pp. 195-199, 1962.

Haynes, H.E & Witchey, A.L. , Medical Electronics: The Pill That "Talks", DEP, pp. 52-54, Camden, N.J.

(56) References Cited

OTHER PUBLICATIONS

Haynes, H.E & Witchey, A.L., Medical Electronics: The Pill That "Talks", DEP, 1960, pp. 52-54, Camden, N.J.
Australian Patent Examination Report No. 1; Endotronix, Inc.; Application No. 2010235020; Date of Issue: Aug. 18, 2014.
Office Action from the Canadian Intellectual Property Office; Endotronix, Inc.; Wireless Sensor Reader; Application No. 2,757,952, Date of Mailing: Oct. 28, 2015.
Notification of the First Office Action from the State Intellectual Property Office of P.R. China; (English Translation) Endotronix, Inc.; Wireless Sensor Reader; Application No. 201080020249.9; Date of Mailing: Apr. 2, 2013.
Notification of the Second Office Action from the State Intellectual Property Office of P.R. China; (English Translation) Endotronix, Inc.; Wireless Sensor Reader; Application No. 201080020249.9; Date of Mailing: Feb. 21, 2014.
Notification of the Third Office Action from the State Intellectual Property Office of P.R. China; (English Translation) Endotronix, Inc.; Wireless Sensor Reader; Application No. 201080020249.9; Date of Mailing: Nov. 2, 2014.
Decision of Rejection from the State Intellectual Property Office of P.R. China; (English Translation) Endotronix, Inc.; Wireless Sensor Reader; Application No. 201080020249.9; Date of Mailing: May 27, 2015.
Communication pursuant to Article 94(3) EPC from the European Patent Office; Application No. 10 762 085.8-1660; Date of Mailing: Jan. 26, 2015.
Communication pursuant to Article 94(3) EPC from the European Patent Office; Application No. 10 762 085.8-1660; Date of Mailing: Sep. 9, 2015.
Office Action—mailing No. 017790 from the Japanese Patent Office; (English Translation); Patent Application No. 2012-504690; Date of Mailing: Jan. 21, 2014.
Office Action—mailing No. 612064 from the Japanese Patent Office; (English Translation); Patent Application No. 2012-504690; Date of Mailing: Nov. 25, 2014.
Office Action—mailing No. 503764 from the Japanese Patent Office; (English Translation); Patent Application No. 2012-504690; Date of Mailing: Nov. 4, 2015.
Examination Report from Pakistan Patent Office (English Translation); Patent Application No. 189/2011; emailed Jun. 6, 2013.
Intellectual Property Office, Ministry of Economic Affairs Office Action Notice from Taiwan Patent Office (English Translation); Endotronix, Inc.; Patent Application No. 100109414; Issued: Jul. 24, 2014.
Office Action from the USPTO; U.S. Appl. No. 13/860,851; Notification Date Oct. 5, 2015.

* cited by examiner

WIRELESS SENSOR READER

RELATED APPLICATIONS

This non-provisional application is a continuation of U.S. patent application Ser. No. 13/859,444 filed on Apr. 9, 2013, which is a continuation of U.S. patent application Ser. No. 13/423,693 filed on Mar. 19, 2012, which is a continuation of U.S. patent application Ser. No. 12/419,326 filed on Apr. 7, 2009, which is a continuation-in-part of U.S. patent application Ser. No. 12/075,858 filed on Mar. 14, 2008, which claims priority to U.S. Provisional Application No. 60/918,164 filed on Mar. 15, 2007 each of which are incorporated by reference in their entirety.

TECHNICAL FIELD

This invention relates generally to reading passive wireless sensors, and more particularly to a reader circuitry for exciting and sensing data from passive wireless sensors.

BACKGROUND

Passive wireless sensor systems that employ resonant circuit technology are known. These systems utilize a passive wireless sensor in remote communication with excitation and reader circuitry. Often the wireless sensor is implanted at a specific location, such as within the human body, to detect and report a sensed parameter. The sensed parameter varies the resonant circuit frequency of the wireless sensor. The reader device samples the resonant frequency of the wireless sensor to determine the sensed parameter.

U.S. Pat. No. 4,127,110 by Bullara discloses a sensor for measuring brain fluid pressure measurement. U.S. Pat. No. 4,206,762 by Cosman discloses a similar sensor for measuring internal pressure. Specifically, the Cosman patent describes the use of a grid dip system for wirelessly measuring the resonant frequency of the sensor. In addition, the Cosman patent discloses the possibility of a battery powered portable reader device.

Several methods of reading passive wireless sensors have also been described in prior patents. For example, the Cosman patent discloses an external oscillator circuit that uses the implanted sensor for tuning, and a grid dip measurement system for measurement of sensor resonant frequency. U.S. Pat. No. 6,015,386 by Kensey, et al., discloses a reader that excites the passive sensor by transmitting frequency sweeps and uses a phase detector on the transmit signal to detect the time during the sweep where the transmitted frequency matches the resonance frequency of the sensor. U.S. Pat. No. 6,206,835 by Spillman, et al., discloses a medical implant application for reader technology disclosed in U.S. Pat. No. 5,581,248 by Spillman, et al. This reader technology detects a frequency dependent variable impedance loading effect on the reader by the sensor's detected parameter. U.S. Pat. No. 7,432,723 by Ellis, et al., discloses a reader with energizing loops each tuned to and transmitting different frequencies spaced to ensure that the bandwidth of the sensor allows resonant excitation of the sensor. Ellis uses a ring-down response from the appropriate energizing loop to determine the sensor resonant frequency.

Some readers utilize phased-locked-loop ("PLL") circuitry to lock onto the sensor's resonant frequency. U.S. Pat. No. 7,245,117 by Joy, et al. discloses an active PLL circuit and signal processing circuit that adjusts a transmitting PLL frequency until the received signal phase and the transmitting PLL signal phase match. When this match occurs, the transmitting PLL frequency is equal to the sensor resonant frequency.

PLL circuits may incorporate sample and hold (S/H) functions to sample the input frequency and hold the PLL at a given frequency. PLLs with S/H may be used in a variety of applications. For example, U.S. Pat. No. 4,531,526 by Genest discloses a reader that uses a PLL circuit with a S/H circuit to adjust the transmitted frequency of the reader to match the resonant frequency received from the sensor. This is done to maximize sensor response to the next transmission and measures the decay rate of the sensor resonance amplitude to extract the sensor value. U.S. Pat. No. 4,644,420 by Buchan describes a PLL with a S/H used to sample a tape data stream and maintain an appropriate sampling frequency for evaluation of digital data pulses on the tape. U.S. Pat. No. 5,006,819 by Buchan, et al., provides additional enhancements to this concept. U.S. Pat. No. 5,920,233 by Denny describes a high-speed sampling technique using a S/H circuit with a PLL to reduce the charge pump noise from the phase-frequency detector to enhance the low-jitter performance of a frequency synthesizing circuit. U.S. Pat. No. 4,511,858 by Charvit, et al., discloses a PLL with a S/H circuit to pre-position the control voltage of a voltage controlled oscillator when the PLL lock frequency is being changed. This is done to enhance the response speed of the PLL when changing the desired synthesized frequency. U.S. Pat. No. 6,570,457 by Fischer and U.S. Pat. No. 6,680,654 by Fischer, et al., disclose a PLL with S/H circuitry to enhance PLL frequency stepping as well as offset correction feature. U.S. Pat. No. 3,872,455 by Fuller, et al. discloses a PLL having a digital S/H to freeze the frequency display and preload the frequency counter when a PLL phase lock is detected.

Current designs for passive sensor readers, such as those disclosed above, suffer from a number of deficiencies. Swept frequency sensor readers similar to those described in the Cosman, Kensey, Ellis and Spillman patents require relatively wide bandwidth allowance by the government body regulating radio transmissions. This limits other uses of the spectrum and makes interference a potential issue. Readers that track the resonant frequency of a passive resonant sensor with a variable frequency transmitter, such as Genest, Ellis, and Joy also suffer from similar problems. Moreover, the amount of electrical power needed for transmissions, signal processing, sampling, and tracking the resonant frequency of a sensor using digitally controlled frequency tracking or swept frequency systems is significant and limits the ability to use battery power in a reader, as well as limiting the longevity of batteries in a battery powered reader. Accordingly, an improved passive sensor reader is needed in the art.

BRIEF DESCRIPTION OF THE DRAWINGS

Reference to the detailed description is taken in connection with the following illustrations.

SUMMARY

A reader device is provided to interface with a wireless sensor. The reader emits a short pulse of energy or a short burst of radio frequency energy to cause the wireless sensor to ring. Immediately after the transmission, the reader receives and amplifies the sensor signal, then sends the signal to a phase-locked loop ("PLL") that locks to the sensor ring frequency. Once the PLL has locked to the ring frequency, the PLL's voltage controlled oscillator ("VCO") is placed in a hold mode to maintain the VCO frequency at the locked frequency. The VCO frequency is counted to determine the sensor resonant frequency.

DETAILED DESCRIPTION OF THE PREFERRED EMBODIMENTS

Figure 1:
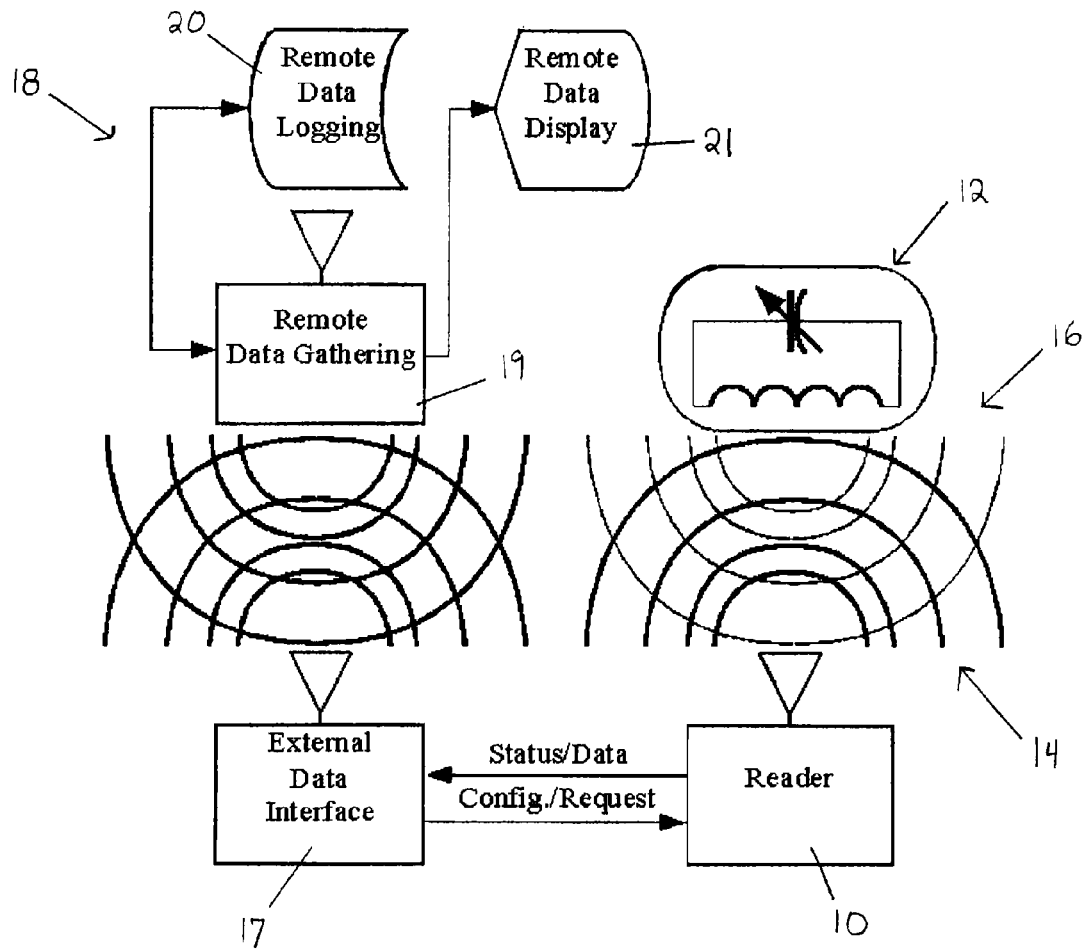
FIG. 1 illustrates a block diagram of a passive wireless sensor system.

A passive wireless sensor system including a reader 10 in remote communication with a sensor 12 is provided. The reader is capable of exciting the sensor 12 by transmitting a signal, such as a radio frequency ("RF") pulse, at or near the resonant frequency of the sensor 12. (See FIG. 1.) The sensor 12 may emit a ring frequency for a short period of time in response to the excitation pulse from the reader 10.

The sensor 12 may be a passive device, capable of emitting a ring signal in response to an excitation signal at or near the resonant frequency of the sensor 12. The sensor 12 may be configured to sense a specific parameter. For example, the sensor 12 may include a fixed inductor and a capacitor that varies based on the sensed parameter. The varying capacitance alters the resonant and ring frequencies of the sensor 12. It should be appreciated, however, that the sensor 12 may be any wireless sensor known in the art capable of remote communication with the reader 10. Further, while the sensor 12 is described as an RF resonant sensor, it will be appreciated that the sensor 12 may be a acoustically resonant sensor, optically resonant sensor, or other similar sensor known in the art. The corresponding reader 10 may employ corresponding signals to activate the sensor 12. Further, the sensor 12 may be an active sensor or a passive sensor.

The reader 10 may excite the sensor 12 by transmitting an excitation pulse 14 in the vicinity of the sensor 12. For example, the reader may emit a radio frequency ("RF") excitation pulse 14 at or near the resonant frequency of the sensor 12. The sensor 12 may emit a ring signal 16 in response to the excitation pulse 14. The reader 10 may determine the frequency of the ring signal 16 in order to determine the sensed parameter value.

The reader 10 may also communicate with a data interface 17. The reader 10 and data interface 17 may be connected directly or indirectly, or may communicate via a remote connection. The reader 10 may send information, such as data related to the sensor 12, to the data interface 17. The reader 10 may further send information regarding the status of the reader 10 to the data interface 17. The data interface 17 may provide configuration information to the reader 10. For example, the data interface 17 may provide information regarding schedules and intervals for sampling the sensor 12.

The data interface 17 may communicate with a remote data system 18 to exchange status and control signals, as well as provide sensor data. The remote data system 18 may include a data gathering module 19 to receive data from the data interface 17, a data logging module 20 to store the received data, and a data display 21 to display the sensor data.

Figure 2:
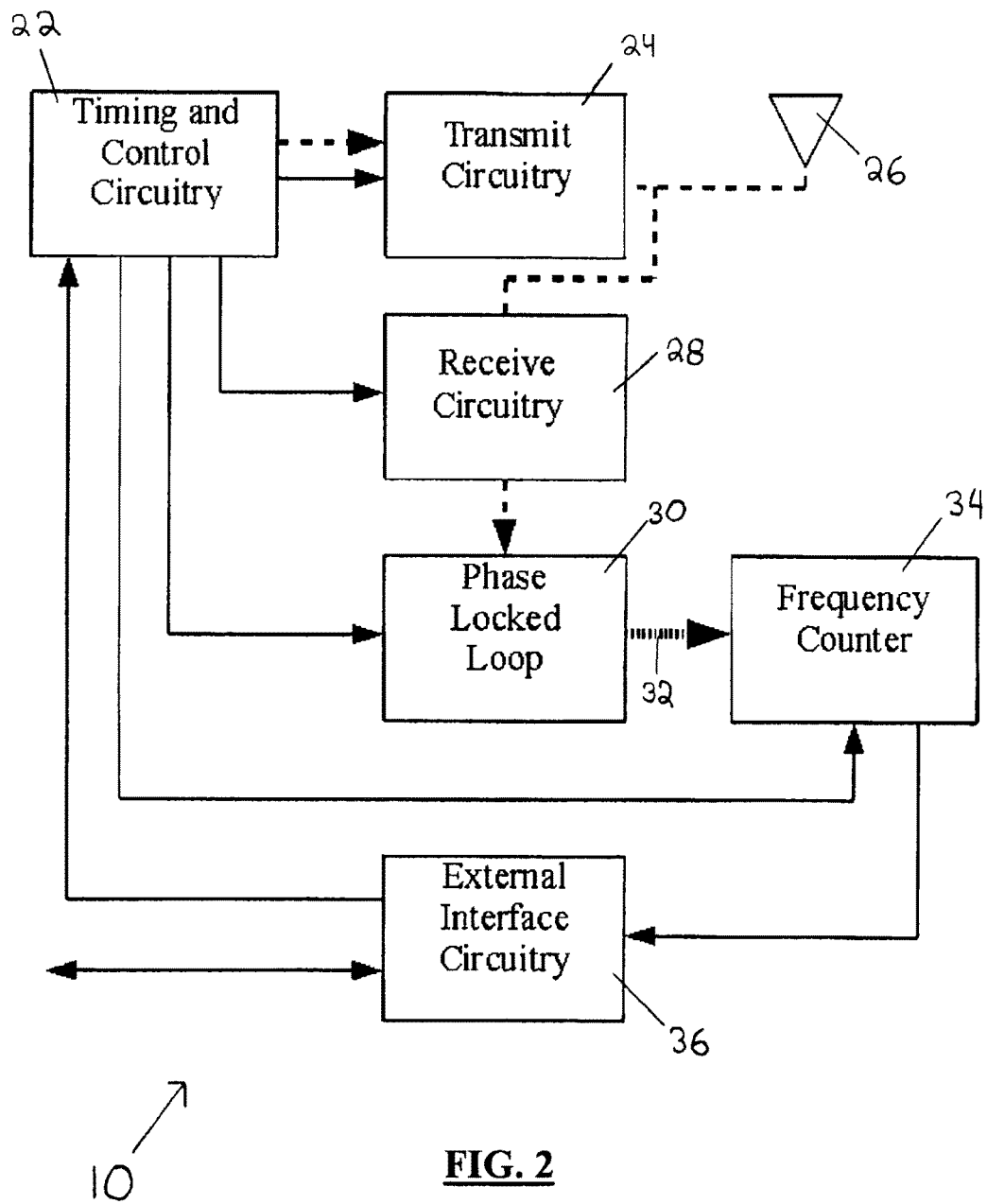
FIG. 2 illustrates a block diagram of the reader circuitry.

The reader 10 includes circuitry to send the excitation pulse 14, receive the ring signal 16, and process the ring signal 16. (FIG. 2.) For example, the reader 10 includes a timing and control circuitry 22 to configure and activate the other circuits in the reader 10. The solid arrows between the timing and control circuitry 22 represent the control interfaces, such as digital or low-frequency signals. The timing and control circuitry 22 further generates an RF signal (illustrated as the broken line arrow) that is sent to a transmit circuitry 24. The transmit circuitry 24 receives the RF signal and sends out the excitation pulse 14 to excite the sensor 12. The timing and control circuitry 22 may only provide the RF signal to the transmit circuitry 24 during the intervals when the excitation pulse is being transmitted to prevent leakage or coupling.

The reader 10 further includes an antenna 26 connected to the transmit circuitry 24 and a receive circuitry 28. The transmit circuitry 24 utilizes the antenna 26 for transmitting the excitation pulse 14, while the receive circuitry 28 utilizes the antenna 26 for receiving the ring signal 16. In an embodiment, the antenna 26 is connected to both the transmit circuitry 24 and the receive circuitry 28 at all times instead of being switched between transmit and receive. This shared antenna 26 design requires special consideration to prevent damage to the receive circuitry 28. Specifically, care must be taken not to overload the very sensitive amplifier stages of the receive circuitry 28. Additionally, the reader 10 requires a fast transition between the extreme overdrive condition present while the transmit circuitry 24 is driving the antenna 26 and the low voltage condition present at the antenna 26 during the receive and amplify phases. For instance, the voltage at the antenna 26 may exceed 200 volts peak-to-peak during transmission of the excitation pulse, and may be single-digit millivolts, decaying rapidly to micro-volts, during reception immediately following the excitation pulse 14. While the reader 10 is described as having a shared antenna 26, it will be appreciated that the reader 10 may incorporate more than one antenna to separately perform the functions of transmitting the excitation pulse 14 and receiving the ring signal 16.

The reader 10 further includes a PLL 30 to receive and lock onto the ring signal 16. The receive circuitry 28 may amplify and condition the ring signal 16 before sending it to the PLL 30. The PLL 30 includes a voltage controlled oscillator ("VCO") 32 that operates at a frequency higher than the ring signal 16 frequency. The VCO 32 interfaces with a frequency counter 34 which counts the VCO 32 frequency, and provides the count to a external interface circuitry 36 for transfer to the data interface 17. By operating the VCO 32 at a higher frequency than the ring signal 16, the time required to count and record the VCO 32 frequency may be significantly decreased.

Figure 3:
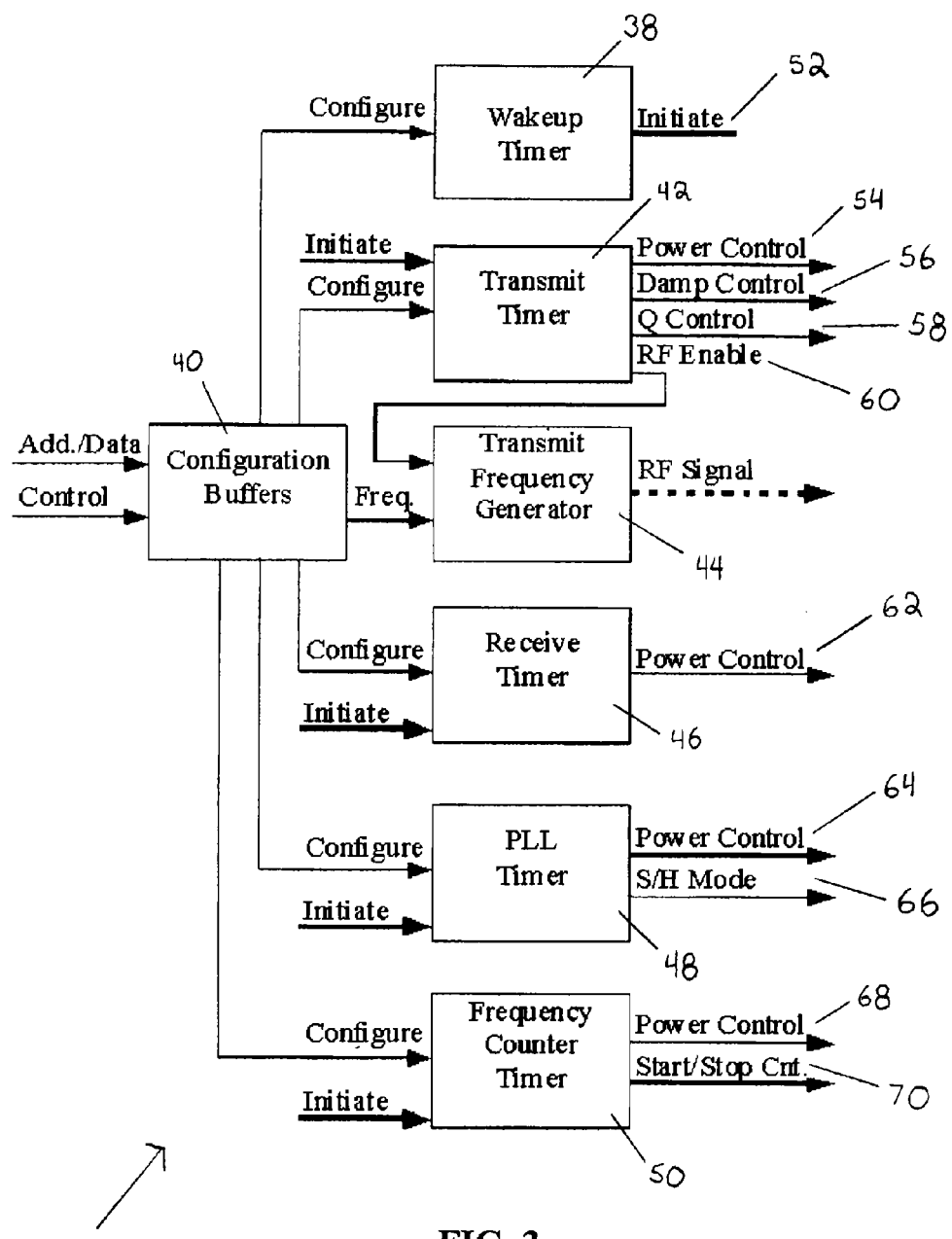
FIG. 3 illustrates a block diagram of the timing and control portion of the reader circuitry.

Each component of the reader 10 is designed to operate efficiently and reduce power consumption. To that end, the reader 10 includes a reduced power mode to conserve power. The timing and control circuitry 22 controls the power status of each component by way of a wakeup timer 38 connected to each component. (FIG. 3.) In reduced power mode, some components may be completely powered down while other components may operate in a sleep mode where power remains to maintain configuration but the circuit becomes static to minimize power consumption.

The timing and control circuitry 22 may place each component of the reader 10 in a sleep or powered-down mode after a specified period of inactivity, such as a few milliseconds when the reader 10 is not sampling the sensor 12. However, it will be appreciated that the specified period of time before entering into reduced power mode may be adjustable. For example, the timing and control circuitry 22 may include a configuration buffer 40 that receives timing instructions from the external interface circuitry 36. The instructions establish the timing period before entering into reduced power mode, and other timing periods for the wakeup timer 38.

The wakeup timer 38 may wake up each component of the reader 10 at the appropriate time to ensure that each component is in an operational state when needed. Specifically, the wakeup timer 38 may communicate with a transmit timer 42, a receive timer 46, a PLL timer 48, and a frequency counter timer 50 to wake up and control the respective components of the reader 10. Once initiated, each of these timers may control and power up the respective component. When configured, the wakeup timer 38 may delay for a specified interval, which may be zero seconds, before sending an initiate signal 52 to start the other timers. As illustrated in FIG. 3, the initiate signal 52 is not shown as a continuous line from the wakeup timer 38 to the respective timers in order to prevent line crossings and minimize confusion.

Once initiated, the transmit timer 42 establishes proper sequence and period to the power control 54, damp control 56, Q control 58, and RF enable 60 signals to properly sequence the transmit circuitry 24 and transmit frequency generator 44. The power control signal 54 controls the power status and sleep status of the transmit circuitry 24. The damp control signal 56 controls the activation of a damping circuit in the transmit circuitry 24 to quickly dissipate antenna 26 energy at the end of a transmission period. The Q control signal 58 controls a switching circuit in the transmit circuitry 24 to reduce the Q of the antenna 26 during reception of the ring signal 16. The RF enable signal allows the transmit frequency generator 44 to send an RF signal to the transmit circuitry 24. In an embodiment, the transmit frequency generator 44 only provides the RF signal to the transmit circuitry 24 during periods where the transmit circuitry 24 is transmitting an excitation pulse 14.

The receive timer 46 is configured to establish proper sequence and period to the power control signal 62 to properly sequence the receive circuitry 28.

The PLL timer 48 establishes proper sequence and period to the power control 64 and S/H mode 66 signals to properly sequence the PLL 30. The power control signal 64 controls the power status and sleep status of the PLL 30. The S/H mode signal 66 controls a sample and hold circuit in the PLL 30, used to cause the PLL to lock onto the transmitted frequency then onto the ring signal 16 frequency, then hold the VCO 32 frequency at the locked frequency until counting is complete.

The frequency counter timer 50 establishes proper sequence and count interval to the power control 68 and start/stop count 70 signals to properly sequence the frequency counter 34. The power control signal 68 controls the power status and sleep status of the frequency counter 34. The start/stop count signal 70 controls the time that the frequency counter 34 begins and ends counting the VCO 32 frequency.

Figure 4:
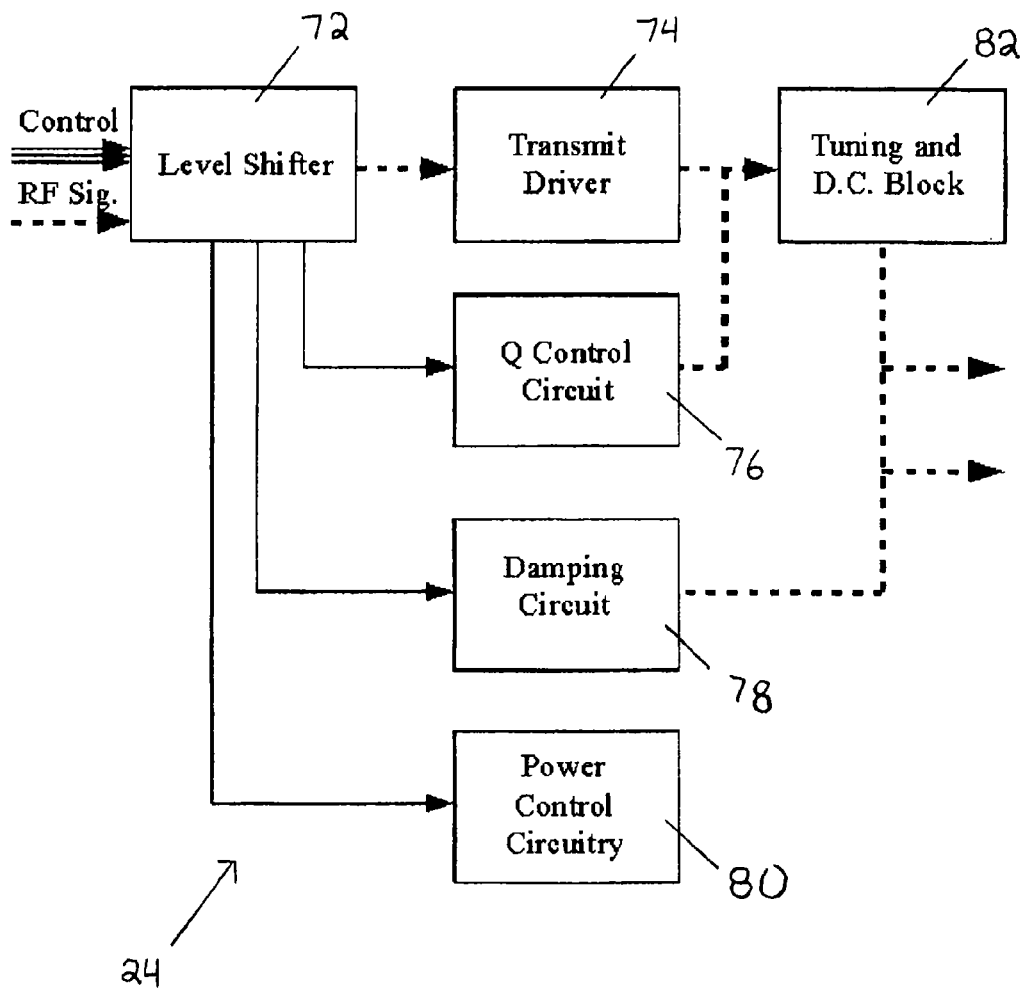
FIG. 4 illustrates a block diagram of the transmit portion of the reader circuitry.

The transmit circuitry 24 is configured to transmit the excitation pulse 14 to the sensor 12 by way of the antenna 26. (FIG. 4.) The excitation pulse 14 may be a fixed or rapidly varying frequency burst at or near the resonant frequency of the sensor 12. For example, the excitation pulse 14 may be a fixed frequency burst within several bandwidths of the sensor 12 resonant frequency. Alternatively, the excitation pulse 14 may be a fixed or rapidly varying frequency burst or sweep of a very short duration at or near a frequency harmonically related to the sensor 12 resonant frequency. The excitation pulse 14 may also be an ultra-wide band pulse. This plurality of excitation pulse 14 approaches is effective because the ring signal 16 is received when the excitation pulse 14 transmissions have ceased. Therefore, excitation pulse 14 transmissions may be limited to frequency bands, amplitudes, and modulation schemes acceptable to regulatory government bodies. Radio frequency regulations generally may not apply to the sensor 12 as the sensor 12 is a purely passive device.

The excitation pulse 14 does not require significant transmission time because a single short transmission of energy results in a single and complete sample of the ring signal 16. Power consumption may be reduced by using a lower transmission duty cycle, thereby reducing the duty cycle of transmit, receive, counting, and digital processing circuitry. By reducing power consumption battery power becomes a much more viable option to power the system.

The excitation pulse 14 may be configured to maximize several system parameters. For example, if a fixed frequency excitation pulse 14 is used, the frequency of the burst may be configured to maximize parameters such as maximum allowable transmit peak power, maximum freedom from in-band or near-band interference during the "receive" interval while the PLL is being locked to the ring signal 16, maximum worldwide acceptance of a particular frequency for reader transmissions for the desired sensor purpose, or other such criteria.

A level shifter 72 of the transmit circuitry 24 receives control signals 54, 56, 58 and the RF signal 60 from the timing and control circuitry 22. The level shifter 72 buffers the inputs and convert control logic levels to circuit drive levels. A transmit driver 74 amplifies the RF signal 60 to provide sufficient power to drive the antenna 26. The Q control circuit 76 is activated during receive to reduce the Q of the combined antenna 26 and tuning and D.C. block 82. A damping circuit 78 is briefly activated immediately at the end of transmission of the excitation pulse 14 to absorb energy in the antenna and allow the antenna to respond to the ring signal 16. The damping circuit 78 may provide a different Q factor to the antenna to improve reception of the ring signal 16. The power control circuitry 80 controls the power-on and sleep mode for components in the transmit circuitry 24. The tuning and D.C. block 82 adjusts tuning for the antenna 26 and prevents direct current from improperly biasing the damping circuit 78. The RF output or excitation pulse 14 from the transmit circuitry is routed to both the antenna 26 and the receive circuitry 28.

Figure 5:
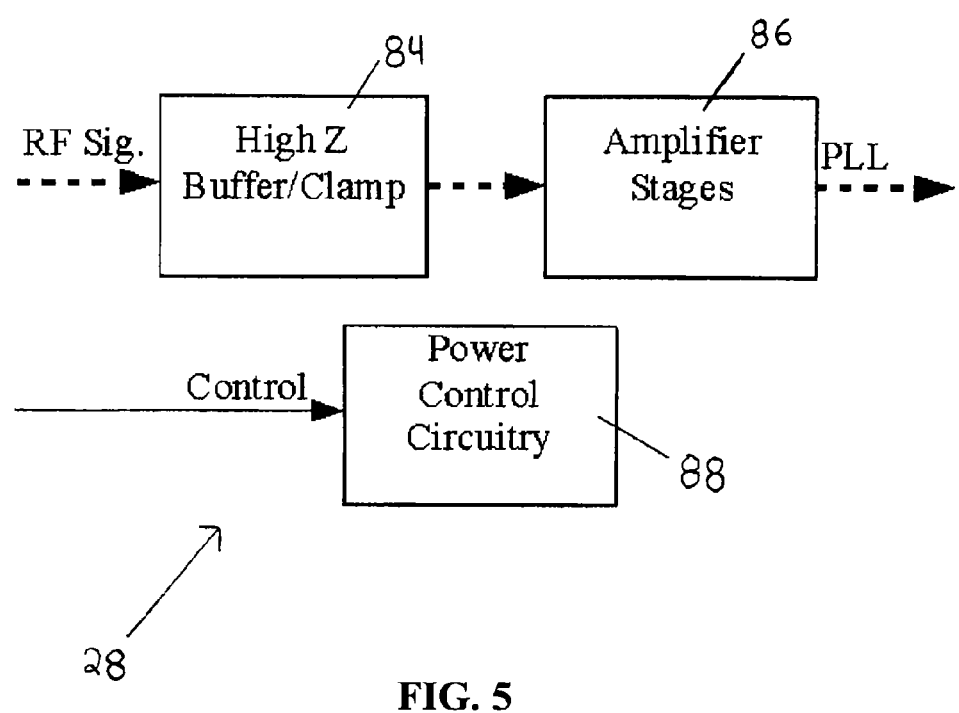
FIG. 5 illustrates a block diagram of the receive portion of the reader circuitry.

Once the excitation pulse 14 is transmitted by the transmit circuitry 24, the receive circuitry 28 is configured to listen for the ring signal 16. With reference to FIG. 5, a high Z buffer/clamp 84 includes a high impedance ("high Z") input device that limits the effect of the receive circuitry 28 on the tuning performed by the tuning and D.C. block 82. The high Z buffer/clamp 84 further serves to protect the amplifier stages 86 from the extreme voltages present on the antenna 26 during transmission of the excitation pulse 14. Voltages at the antenna 26 may reach upwards of 200 volts peak-to-peak during transmission of the excitation pulse, requiring only approximately 60 pico-farads of capacitance to tune the antenna 26. In an embodiment, a 1 pico-farad capacitor is used as a high impedance input current limiting device on a 13.5 mega-hertz transmit circuit. Low capacitance diode junctions that shunt over-voltage to the power supply and under-voltage to ground may be used as clamping devices.

The amplifier stages 86 amplify the ring signal 16 to a sufficient level to drive the PLL 30 input. Careful design of the amplifier stages 86 is required to achieve adequate transient response when the transmitted excitation pulse 14 signal is removed and damped, and the low level ring signal 16 is received. Common gate amplifier stages with low Q tuned reactive drain loads may be used to condition the high Z buffer/clamp 84 output, followed by several filters interspersed between high gain amplifier stages. The filters may be either resistor-capacitor ("RC") filters or inductor-capacitor ("LC") filters. In an embodiment, the filters may all be RC bandpass filters. Another common gate amplifier stage with low Q tuned reactive drain load may be used for final bandpass conditioning prior to feeding the signal to the PLL 30 input. This design enables all of these amplifier types to perform from extremely low signal input levels to extremely high signal input levels without signal distortion such as frequency doubling or halving due to stage saturation characteristics, as well as the excellent high input impedance achievable with the common-gate amplifier stages and the outstanding transient response characteristics of the RC filter interspersed between high gain amplifier stages. Special care must be taken in stage-to-stage power and signal isolation to prevent unwanted oscillations due to the extreme gain associated with the amplifier stages 86.

Power control circuitry 88 may apply and remove power to and from the amplifier stages 86 and the buffer in the high Z buffer/clamp 84 to reduce power consumption. It should be noted that the high Z buffer/clamp 84 is designed to provide full protection even with power removed as excess energy will merely power up the amplifier stages 86 until dissipated. The input impedance is high enough to limit excess energy to prevent overpowering the amplifier stages 86. In an embodiment, the receive circuitry 28 is active during the transmission of the excitation pulse 14 to decrease the time required for the PLL 30 to lock onto the ring signal 16.

Figure 6:
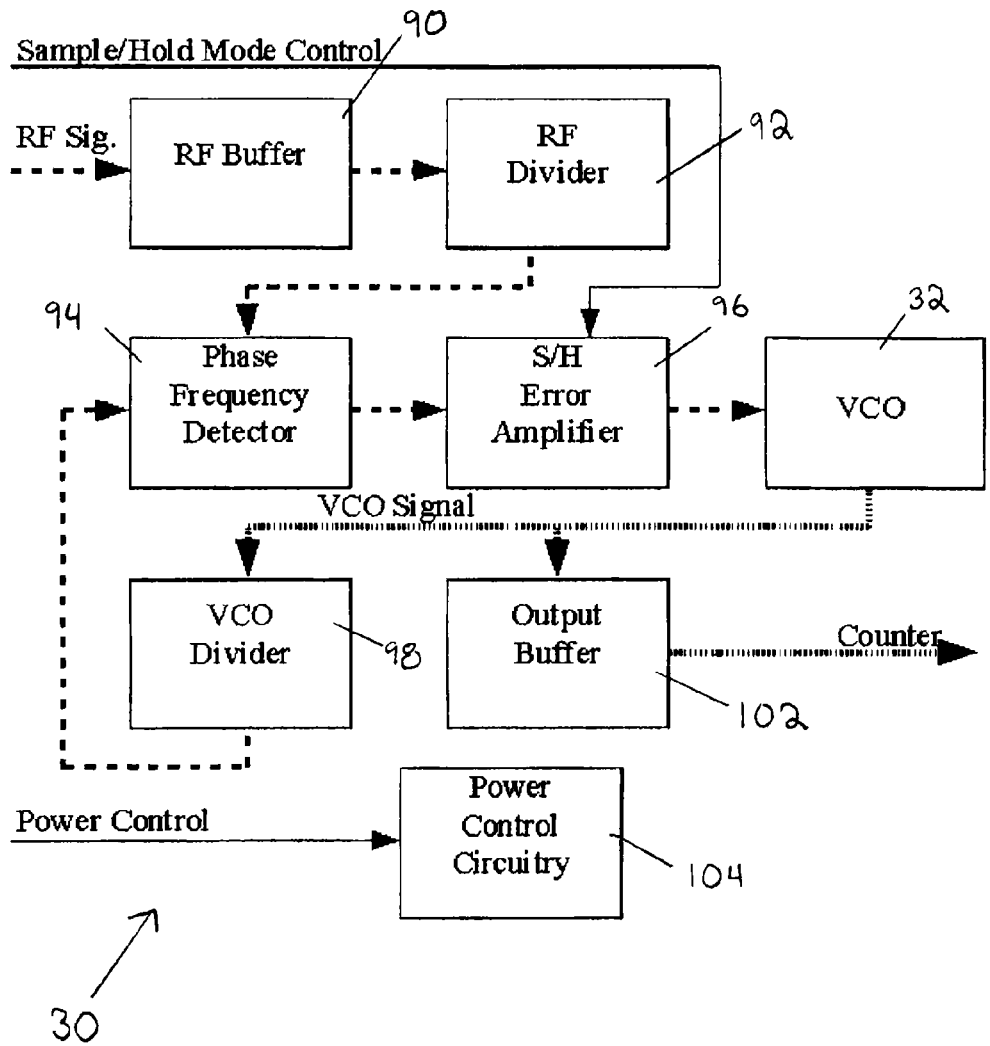
FIG. 6 illustrates a block diagram of the phase locked loop portion of the reader circuitry.
Figure 7:
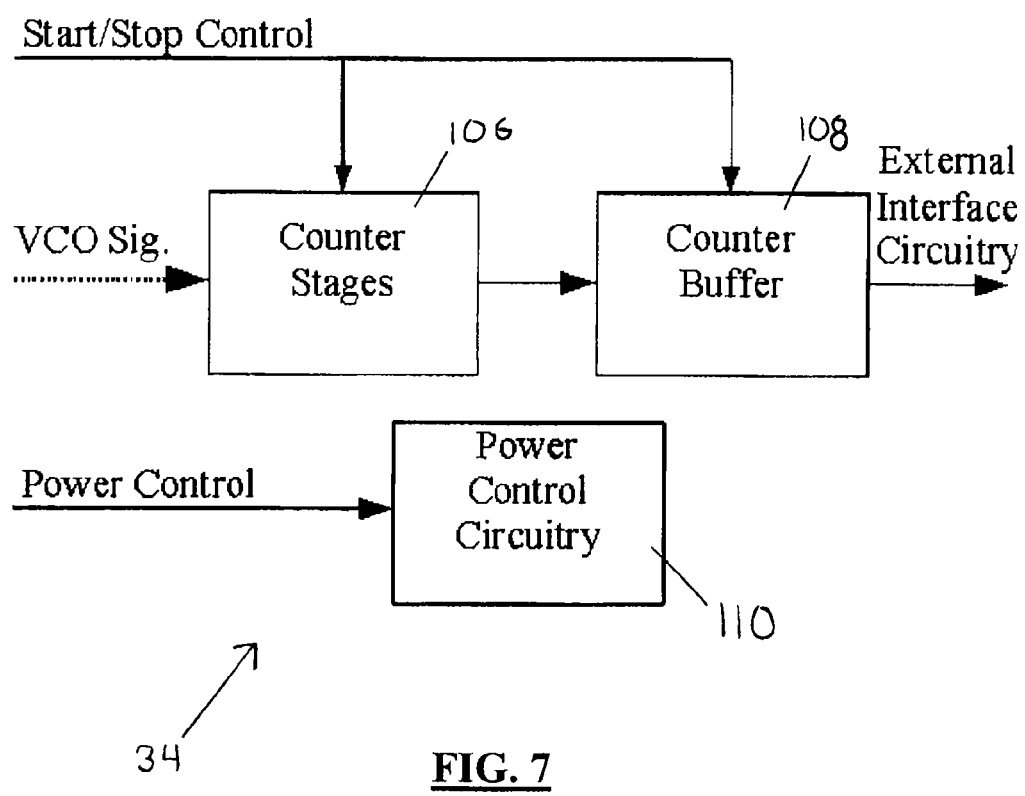
FIG. 7 illustrates a block diagram of the frequency counter portion of the reader circuitry.

The PLL 30 receives the amplified and conditioned ring signal 16 from the receive circuitry 28. With reference to FIGS. 5 and 6, the RF signal from the receive circuitry 28 amplifier stages 86 feeds an RF buffer 90 of the PLL 30. The RF buffer 90 may feed the RF signal to an optional RF divider 92 that divides the RF signal frequency by an integer value. (FIG. 6.) The RF divider 92 then feeds the RF signal to a first input of a phase frequency detector 94. The output of the frequency detector 94 feeds a sample-and-hold (S/H) error amplifier 96. The S/H error amplifier 96 controls the frequency of the VCO 32. The output of the VCO 32 feeds the VCO divider 98, which output in turn feeds a second input to the phase frequency detector 94. The PLL 30 may include an output buffer 102 to reduce loading of the VCO 32 while forwarding the VCO signal frequency to the frequency counter 34. The VCO divider 98 allows the VCO 32 to operate at a frequency significantly higher than the ring frequency 16. As a result, the time required to count and record the VCO signal frequency may be significantly reduced. Moreover, the shorter count interval reduces VCO drift during counting and allows a higher sample rate.

The phase frequency detector 94 is configured to determine the frequency and phase error between the divided RF signal and the divided VCO signal. This is best accomplished by filtering and amplifying the RF signal that is fed to the S/H error amplifier 96. Further, the S/H feature may optimally forward the filtered and amplified signal to control the VCO 32. In this manner, a closed control loop is formed that causes the VCO 32 frequency to equal to the ring signal 16 frequency times the VCO divider 98 integer divided by the RF divider 92 integer. The PLL 30 may include additional frequency dividers to optimize the circuit design and increase the potential VCO 32 frequency range.

The PLL timer 48 sends a S/H mode control signal 66 to the S/H error amplifier 96 of the PLL 30. The S/H mode control signal 66 may place the VCO 32 in a sample mode. In an embodiment, the VCO 32 is placed in sample mode for a predetermined length of time. In sample mode, the VCO signal frequency is adjusted to match the ring signal frequency, as described above. When the S/H mode control signal 66 is placed in the hold mode, the S/H error amplifier 96 will hold its output constant, causing the control voltage to the VCO 32 to be approximately constant over a length of time sufficient to count the VCO signal frequency.

The power control signal from the PLL timer 48 to the power control circuitry 104 determines whether the PLL 30 is in a power on or a sleep/power-off mode to conserve electrical power. Depending on the specific PLL that is used, a control and communication link (not shown) may be required to set the RF divider 92 integer, the VCO divider 98 integer, and the phase frequency detector 94 outputs and output configurations. The communications link may be specific to the particular PLL 30 used.

The frequency counter 34 includes counter stages 106, a counter buffer 108, and a power control circuitry 110. The frequency counter timer 50 sends a start/stop control input to the counter stages 106 and counter buffer 108. The frequency counter timer 50 also sends a power control input to the power control circuitry 110. The counter stages 106 count the VCO signal frequency from the PLL 30 output buffer 102. The counter stages 106 start counting when the start/stop control commands start, and end when the start/stop control commands stop. When the start/stop control commands stop, the counter buffer 108 is loaded with the count value from the counter stages 106. The power control circuitry 110 controls the power-on and sleep modes for components in the frequency counter 34. The counter buffer 108 output may supply a count input to the external interface circuitry 36. The ring frequency 16, and subsequently the sensed parameter, may be determined from the frequency count.

In operation, the reader 10 sequences as follows. During periods of time when the sensor 12 is not being sampled, all components of the reader 10 are placed in reduced power mode. The wakeup timer 38 in the timing and control circuitry 22 is configured for a particular sample delay or sample interval. At the specified time, the wakeup timer 38 initiates a sample sequence. Specifically, the wakeup timer 38 powers up or wakes up each component of the reader at appropriate times to ensure each component is in an operational state when needed.

The external interface circuitry 36 consumes minimal power when not actively communicating so is maintained in a ready condition at all times. The timing and control circuitry 22 provides the RF signal to the transmit circuitry 24 for a short period of time, such as approximately 20 microseconds. The RF signal from the timing and control circuitry 22 is then secured and the transmit circuitry 24 is controlled to damp the antenna 26 quickly. The transmit circuitry 24 is then placed in an appropriate mode to allow reception of the ring signal 16 at the antenna 26. In an embodiment, when the antenna 26 is configured to receive the ring signal 16, the antenna 26 damping is greater than the ring signal 16 damping.

During transmission of the excitation pulse 14, the receive circuitry 28 receives, conditions, and clamps the transmitted RF signal at the antenna 26. Once transmission of the excitation pulse 14 ceases and the antenna 26 is configured to receive the ring signal 16, the receive circuitry transitions into a high-gain reception mode to receive the ring signal 16 from the antenna 26. The PLL 30 is in sample mode to allow the RF buffer 90 to receive the conditioned output of the receive circuitry 28. When the antenna 26 begins to receive the ring signal 16, the PLL 30 shifts from locking onto the transmitted excitation pulse 14 frequency to locking onto the ring signal 16 frequency. After a time interval sufficient for the PLL 30 to lock onto the ring signal 16 frequency, the PLL 30 is shifted to hold mode to maintain VCO 32 frequency at ring signal 16 frequency. The receive circuitry 28 and transmit circuitry 24 are powered down or placed in sleep mode as appropriate.

Once the PLL 30 is in hold mode, the timing and control circuitry 22 instructs the frequency counter 34 to conduct a controlled interval count of the VCO 32 frequency. Upon completion of the count, the PLL 30 components are powered down or placed in sleep mode as appropriate and the count value is transferred to the external interface circuitry 36. The frequency counter 34 components are then powered down or placed in sleep mode as appropriate, and subsequently the timing and control circuitry 22 components are powered down or placed in sleep mode as appropriate. If programmed for interval sampling, the timing and control circuitry 22 wakeup timer 38 counts until the next sample is due. Otherwise, the timing and control circuitry 22 awaits a wakeup command with any other needed instructions from the external interface circuitry 36.

The embodiment of the invention has been described above and, obviously, modifications and alternations will occur to others upon reading and understanding this specification. The claims as follows are intended to include all modifications and alterations insofar as they are within the scope of the claims or the equivalent thereof.

The invention claimed is:

1. A wireless sensor reader comprising:
   a transmit circuit configured to generate at least one excitation pulse to cause a passive wireless sensor to emit at least one response signal;
   at least one antenna configured to transmit said excitation pulse and receive said response signal;
   a phase-locked loop circuit configured to receive said response signal from said at least one antenna, said phase-locked loop circuit including a voltage-controlled oscillator configured to generate a count signal at a frequency related to said response signal frequency, wherein said voltage-controlled oscillator operates at a frequency higher than said at least one response signal;
   a first circuitry configured to sample the control voltage input of said voltage-controlled oscillator;
   a second circuitry configured to generate a control voltage signal for input to said voltage-controlled oscillator; and
   wherein said passive wireless sensor is configured to change its resonant frequency in proportion to at least one sensed parameter.

2. The wireless sensor reader of claim 1, wherein said first circuitry further comprises analog-to-digital conversion circuitry.

3. The wireless sensor reader of claim 2, wherein the value obtained from said analog-to-digital conversion circuitry is used to configure said phase-locked loop circuit to said hold mode.

4. The wireless sensor reader of claim 1, wherein said second circuitry further comprises digital-to-analog conversion circuitry.

5. The wireless sensor reader of claim 1, further comprising a switch for selecting the input to said voltage-controlled oscillator from between said generated control voltage signal and the output of the phase detector of said phase-locked loop.

6. The wireless sensor reader of claim 1, wherein said reader is configured to hold said voltage-controlled oscillator frequency at a generated fixed frequency during at least a portion of the time when said response signal is not present.

7. The wireless sensor reader of claim 1, wherein said control voltage input of said voltage-controlled oscillator that corresponds to said count signal frequency is output directly from said phase-locked loop circuit.

8. The wireless sensor reader of claim 1, wherein said phase-locked loop circuit further includes circuitry for internal calibration.

9. The wireless sensor reader of claim 8, wherein said calibration circuitry enables said control voltage input of said voltage-controlled oscillator to be correlated with said response signal frequency.

10. The wireless sensor reader of claim 9, wherein said calibration circuitry enables the introduction of a reference signal into said phase-locked loop in place of said response signal.

11. The wireless sensor reader of claim 9, wherein said calibration circuitry enables the introduction of a reference voltage into said voltage controlled oscillator in place of said control voltage input, and the evaluation of said voltage-controlled oscillator output frequency.

12. The wireless sensor reader of claim 1 wherein said wireless sensor reader is further configured to measure said reference response signal frequency and utilizes it to improve the accuracy of the reading obtained from said wireless sensor.

13. The wireless sensor reader of claim 1 wherein said phase-locked loop circuit is capable of being placed in a sample mode to receive said response signal and adjust the frequency of said count signal based on the frequency of said response signal.

14. The wireless sensor reader of claim 1, wherein said voltage-controlled oscillator is in communication with a calibration circuit wherein said voltage-controlled oscillator is calibrated during a portion of the time when said response signal is not present.

15. A wireless sensor reader comprising:
   a transmit circuit configured to generate at least one excitation pulse to cause a passive wireless sensor to emit at least one response signal corresponding to a sensed parameter value;
   at least one antenna configured to transmit said at least one excitation pulse and receive said at least one response signal;
   a receive circuit for amplifying said at least one received response signal;
   a phase-locked loop circuit configured to receive said response signal from said at least one antenna, said phase-locked loop circuit including a voltage-controlled oscillator configured to generate a count signal at a frequency related to said response signal frequency, wherein said voltage-controlled oscillator operates at a frequency higher than said at least one response signal;

a first circuitry configured to sample the control voltage input of said voltage-controlled oscillator;

a second circuitry configured to generate a control voltage signal for input to said voltage-controlled oscillator; and a timing and control circuitry to configure and activate at least said transmit circuit and said receive circuit.

16. The wireless sensor reader of claim 15 wherein said wireless sensor reader is a handheld device.

17. The wireless sensor reader of claim 15 further comprising a battery for powering said wireless sensor reader.

18. A system for reading a passive wireless sensor comprising:

a passive wireless sensor including at least one inductor and one capacitor configured to change its resonant frequency in proportion to at least one sensed parameter; and a reader for transmitting at least one excitation pulse to said passive wireless sensor and to receive at least one signal from said passive wireless sensor in response to said excitation pulse, wherein the reader includes:

a phase-locked loop circuit configured to receive said response signal from said at least one antenna, said phase-locked loop circuit including a voltage-controlled oscillator configured to generate a count signal at a frequency related to said response signal frequency, wherein said voltage-controlled oscillator operates at a frequency higher than said at least one response signal;

a first circuitry configured to sample the control voltage input of said voltage-controlled oscillator;

a second circuitry configured to generate a control voltage signal for input to said voltage-controlled oscillator; and a timing and control circuitry to configure and activate at least said transmit circuit and said receive circuit.

19. The wireless sensor reader of claim 15 wherein said timing and control circuitry places each component of the reader in a powered-down mode after a specified period of inactivity.

20. The wireless sensor reader of claim 15 wherein said timing and control circuitry further comprises a wakeup timer to communicate with a transmit timer, a receive timer, a PLL timer, and a frequency counter timer to wake up and control the respective components of the wireless sensor reader.

* * * * *